(12) United States Patent
Ishii et al.

(10) Patent No.: US 7,820,416 B2
(45) Date of Patent: Oct. 26, 2010

(54) PROCESS FOR PRODUCING AMIDE COMPOUND AND ACRYLAMIDE POLYMER

(75) Inventors: Katsuo Ishii, Yokohama (JP); Kozo Murao, Yokohama (JP)

(73) Assignee: Dia-Nitrix Co., Ltd., Tokyo (JP)

( * ) Notice: Subject to any disclaimer, the term of this patent is extended or adjusted under 35 U.S.C. 154(b) by 0 days.

(21) Appl. No.: 11/813,376

(22) PCT Filed: Dec. 28, 2005

(86) PCT No.: PCT/JP2005/024077

§ 371 (c)(1),
(2), (4) Date: Jul. 5, 2007

(87) PCT Pub. No.: WO2006/073110

PCT Pub. Date: Jul. 13, 2006

(65) Prior Publication Data

US 2008/0108770 A1    May 8, 2008

(30) Foreign Application Priority Data

Jan. 7, 2005    (JP) ............................ P2005-002569

(51) Int. Cl.
*C12P 13/02* (2006.01)
(52) U.S. Cl. .................... 435/129; 435/128; 435/170
(58) Field of Classification Search .............. 435/128, 435/129, 170
See application file for complete search history.

(56) References Cited

U.S. PATENT DOCUMENTS

| | | | | |
|---|---|---|---|---|
| 3,238,883 A | * | 3/1966 | Martin | 417/299 |
| 3,493,609 A | * | 2/1970 | Kronig et al. | 562/524 |
| 6,518,684 B1 | * | 2/2003 | Schaich et al. | 310/103 |
| 6,544,019 B2 | * | 4/2003 | Martin et al. | 418/69 |
| 7,267,524 B2 | * | 9/2007 | Yu | 415/55.1 |
| 7,309,590 B2 | * | 12/2007 | Petersen et al. | 435/129 |
| 2004/0048348 A1 | | 3/2004 | Murao et al. | |
| 2007/0027294 A1 | | 2/2007 | Murao et al. | |
| 2007/0071616 A1 | * | 3/2007 | Owen et al. | 417/410.4 |

FOREIGN PATENT DOCUMENTS

| | | |
|---|---|---|
| JP | 2 19673 | 1/1990 |
| JP | 9 118704 | 5/1997 |
| JP | 10 316714 | 12/1998 |
| JP | 2000-354497 | 12/2000 |
| JP | 2001 78749 | 3/2001 |
| JP | 2001 299376 | 10/2001 |
| JP | 2004 524047 | 8/2004 |
| RU | 2 057 145 1 | 3/1996 |
| RU | 2 057 145 C1 | 3/1996 |
| RU | 2 060 258 C1 | 5/1996 |
| WO | 00/65079 | 11/2000 |
| WO | 01/78913 A1 | 10/2001 |
| WO | 02 088373 | 11/2002 |
| WO | 2004/090148 A1 | 10/2004 |

OTHER PUBLICATIONS

Krainev, A.F., Mechanics of machines, Fundamental dictionary, Moscow, Mechnical Engineering, p. 390 "pump"; p. 391 "gear-type pump", schemas a) and b) (2000)(with English translation).
Decision on Grant for RU 2007129749 (w/English translation).
Krainev, A.F., Mechanics of machines, Fundamental dictionary, Moscow, Mechnical Engineering, p. 390 "pump"; p. 391 "gear-type pump", schemas a) and b) (2000)(with English translation).
S. Xudong, et al., Biochemical Engineering Journal, vol. 18, No, 3, pp. 239-243 (2004).

* cited by examiner

*Primary Examiner*—Helen L. Pezzuto
(74) *Attorney, Agent, or Firm*—Oblon, Spivak, McClelland, Maier & Neustadt, L.L.P.

(57) ABSTRACT

In a method for producing an amide compound of the present invention including obtaining an amide compound from a nitrile compound using a microbial catalyst and transferring a solution containing the microbial catalyst and the amide compound, a positive-displacement pump is used for transferring the solution containing a microbial catalyst and an amide compound to obtain an amide compound having few impurities. A monomer including (meth)acrylamide obtained by the method for producing an amide compound is polymerized to prepare an acrylamide polymer having a high-molecular mass and high solubility and being colorless.

10 Claims, No Drawings

PROCESS FOR PRODUCING AMIDE COMPOUND AND ACRYLAMIDE POLYMER

TECHNICAL FIELD

The present invention relates to a method for producing an amide compound such as (meth)acrylamide with the aid of a microbial catalyst and an acrylamide polymer.

Priority is claimed on Japanese Patent Application No. 2005-002569, filed on Jan. 7, 2005, the content of which is incorporated herein by reference.

BACKGROUND ART

Acrylamide polymers are applied to coagulants, thickeners for paper making, and the like. For each use, an acrylamide polymer having high-molecular mass, high solubility, and almost colorless color tone has been desired.

For example, if a low-molecular mass acrylamide polymer is used as a coagulant, the acrylamide polymer imparts an insufficient aggregative property. If an acrylamide polymer having poor solubility is used as a coagulant, a problem of delay of treatment time is arisen. If an acrylamide polymer having poor solubility is used as a thickener for paper making, a defect such that fish-eye generates on the paper occurs. When the acrylamide polymer is used as a thickener for paper making, as a matter of course, it is necessary to use an acrylamide polymer having almost colorless color tone.

Under such a condition, regarding improvement of the solubility of an acrylamide polymer, it has been found that acrylamide is produced and an acrylamide polymer is produced by using the acrylamide as a raw material after removing impurities in acrylonitrile. Regarding a method for producing acrylamide, it is known that an enzymic method using a microbial catalyst is preferably adopted (for example, see Patent Documents 1 and 2).

When acrylamide is produced by the enzymic method, various studies have been carried out for improving the quality of acrylamide polymers. For example, a method of limiting a usage of a catalyst (Patent Document 3), and a method of removing impurities derived from a catalyst in a produced acrylamide aqueous solution (Patent Document 4) are known.

However, an acrylamide polymer produced using, as a raw material, acrylamide obtained by the enzymic method using a microbial catalyst has insufficient molecular mass and solubility, and color tone thereof is not colorless.

Regarding the enzymic method, there are almost no reports about a pump to be used when acrylamide is produced. Only Patent Document 5 discloses a method for producing an acrylamide aqueous solution by hydrating a reaction mixture containing acrylonitrile in an aqueous solution while circulating the aqueous solution using a side channel pump (a kind of centrifugal pumps) in the presence of a microbial catalyst.

However, an acrylamide polymer produced using, as a raw material, the acrylamide obtained by the above method has insufficient molecular mass and solubility, and color tone thereof is not colorless.

Patent Document 1: Japanese Unexamined Patent Application, First Publication No. H10-316714

Patent Document 2: Japanese Unexamined Patent Application, First Publication No. H9-118704

Patent Document 3: Japanese Unexamined Patent Application, First Publication No. 2001-299376

Patent Document 4: Japanese Unexamined Patent Application, First Publication No. 2001-078749

Patent Document 5: Japanese Unexamined Patent Application, First Publication No. 2004-524047

DISCLOSURE OF INVENTION

Problems to be Solved by the Invention

The object of the present invention is to provide a method for producing an amide compound in which an amide compound containing few impurities can be obtained; and an acrylamide polymer having a high-molecular mass and high solubility, and being almost colorless.

Means for Solving the Problems

The inventors of the present invention have intensively studied to solve the above problem. As a result, they have found that, when acrylamide is produced from acrylonitrile using a microbial catalyst, an acrylamide aqueous solution, which can be a raw material for an acrylamide polymer having high-molecular mass and high solubility, and being colorless, is obtained using a positive-displacement pump such as a screw type pump and a rotary pump instead of a conventional centrifugal pump as a transfer pump of a solution containing the microbial catalyst, and they completed the present invention.

A method for producing an amide compound of the present invention including obtaining an amide compound from a nitrile compound using a microbial catalyst and transferring a solution containing the microbial catalyst and the amide compound, is characterized by using a positive-displacement pump for transferring the solution containing a microbial catalyst and an amide compound.

It is desirable that the nitrile compound be (meth)acrylonitrile and the amide compound be (meth)acrylamide.

Furthermore, an acrylamide polymer of the present invention is provided by polymerizing a monomer containing (meth)acrylamide which is obtained by the method for producing an amide compound of the present invention.

EFFECTS OF THE INVENTION

According to the method for producing an amide compound of the present invention, an amide compound containing few impurities is obtained.

The acrylamide polymer of the present invention has high-molecular mass and solubility, and color tone thereof is almost colorless. This acrylamide polymer has high quality and extremely high availability.

BEST MODE FOR CARRYING OUT THE INVENTION

Method for Producing Amide Compound

The method for producing an amide compound of the present invention includes a step of obtaining an amide compound from a nitrile compound using a microbial catalyst (hereinafter, referred to a "reaction step") and a step of transferring a solution containing the microbial catalyst and the amide compound (hereinafter, referred to as a "transfer step").

(Reaction Step)

In the reaction step, concretely, an amide compound aqueous solution is obtained by hydrating a nitrile compound in water in the presence of a microbial catalyst.

The hydration reaction of the nitrile compound using the microbial catalyst can be carried out at ordinary temperature by a conventional method.

When the nitrile compound is acrylonitrile, the hydration reaction is carried out as follows.

Water and the microbial catalyst are provided in a reaction container, the solution is adjusted to be pH 5 to 9.5 and 5.5 to 50° C., and then acrylonitrile is added as a substrate to the solution. Preferably, acrylonitrile is continuously added so that a concentration of acrylonitrile in the reaction solution is 0.1 to 10% by mass. The hydration reaction is maintained until acrylonitrile is no longer detected in the reaction solution. The hydration reaction is maintained until the concentration of acrylamide in the reaction solution becomes preferably 30% by mass or more, more preferably within 40 to 60% by weight. After achieving the desired concentration of acrylamide, addition of acrylamide is stopped and the reaction is maintained until acrylonitrile is not detected in the reaction solution.

If acrylamide is produced by maintaining acrylamide in the reaction solution at high concentration, it is more economical and a high quality acrylamide polymer can be produced.

(Microbial Catalyst)

A "microbial catalyst" in the present invention is a microorganism containing nitrilehydratase. "Nitrilehydratase" is an enzyme which converts a nitrile compound to a corresponding amide compound. Examples of nitrilehydratase include nitrilehydratase derived from microorganisms belonging to such as *Bacillus, Bacteridium, Micrococcus, Brevibacterium, Corynebacterium, Nocardia, Pseudomonas, Rhodococcus, Microbacterium, Rhodococcus rhodochrous* sp, *Fusarium*, and *Agrobacterium*.

A nitrlehydratase gene derived from the above microorganisms is obtained and then the gene as it is may be used or a transformant obtained by artificially improving the gene using a conventional method and introducing the improved gene into an optional host may be used (see "Molecular Cloning 2nd Edition, Cold Spring Harbor Laboratory Press, 1989"). Typical examples of transformants include *Escherichia coli* MT10770 (FERM P-14756) transformed by nitrilehydratase derived from *Achromobacter* bacteria (Japanese Unexamined Patent Application, First Publication No. H8-266277), *Escherichia coli* MT10822 (FERM BP-5785) transformed by nitrilehydratase derived from Pseudonocardia bacteria (Japanese Unexamined Patent Application, First Publication No. H9-275978), and a microorganism transformed by nitrilehydratase derived from *Rhodococcus rhodochrous* sp (Japanese Unexamined Patent Application, First Publication No. H4-211379).

Typical examples of forms of microbial catalysts include a culture medium obtained by culturing the above microorganisms according to an ordinary method; a resting microorganism obtained by separating from the culture medium and washing the microorganism as needed; and an immobilized microorganism obtained by immobilizing the resting microorganism to a carrier (for example, polyacrylamide gel, alginate, carrageenan, or the like).

Preparation of the microbial catalyst is, for example, carried out as follows.

In a culture medium in which a carbon source (saccharides such as glucose) and a nitrogen source (for example, an inorganic nitrogen source such as ammonium sulfate, ammonium chloride, and ammonium nitrate; an organic nitrogen source such as yeast extract, peptone, and meat extract), and, as needed, inorganic salts, metal salts, vitamins, and the like are added, a microorganism which produces nitrilehydratase is cultured at 20 to 40° C. with pH 5-9. For the culture conditions, shaking or rotation may be carried out suitably. After culturing, the microorganism is washed with a phosphate buffer or the like to prepare a microbial catalyst. Furthermore, an immobilized microbial catalyst may be obtained by adding a monomer such as acrylamide to the microorganism suspension and polymerizing the monomer.

(Nitrile Compound)

A "nitrile compound" in the present invention is converted to an amide compound by the action of nitrilehydratase. Examples of nitrilehydratases include aliphatic saturated nitrites such as acetonitrile, propionitrile, succinonitrile, and adiponitrile; aliphatic unsaturated nitriles such as benzonitrile and phthalodinitirile; and hetelocyclic nitrites such as 3-cyanopyridine and 2-cyanopyridine. "(Meth)acrylonitrile" of the present invention is defined as acrylonitrile and/or methacrylonitrile.

In view of chemical and physical characteristics, (meth)acrylonitrile and nicotineamide are preferable as a nitrile compound. In view of economy and quality, and in view of production of (meth)acrylamide to be a raw material of high quality acrylamide polymer, (meth) acrylonitrile is more preferable. "(Meth)acrylamide" of the present invention is defined as acrylamide and/or methacrylamide.

(Transfer Step)

As a transfer step, a step of extracting a solution including a microbial catalyst and an amide compound from a reaction container and transferring the solution to a tank or the like or a step of transferring a solution including a microbial catalyst and an amide compound to a filter to separate the microbial catalyst and the amide compound may be used.

(Positive-Displacement Pump)

A "positive-displacement pump" of the present invention is a pump for transferring a liquid by storing the liquid in a space formed in a pump head and pushing the liquid. Examples of positive-displacement pumps include a reciprocating pump, a rotary pump, and a tube pump. A pump such as a centrifugal pump (turbine pump and volute pump) which applies a shearing force to a liquid in the pump head is not included in the positive-displacement pumps.

Among the positive-displacement pumps, in view of industrially stable operation, a reciprocating pump and a rotary pump are preferable, and a rotary pump is particularly preferable.

Examples of rotary pumps include a gear pump, a rotary pump, and a screw pump. Examples of gear pumps include a chemical gear pump and a magnet drive gear pump (manufactured by IWAKI CO., LTD.). Examples of rotary pumps include a Waukesha pump (manufactured by IWAKI CO., LTD.), a sine pump (manufactured by Tokushu Kika Kogyo), and an SX type rotary pump (manufactured by Alfa Laval K.K.). Examples of screw pumps include a screw pump (manufactured by IWAKI CO., LTD.) and a NEMO® pump (manufactured by HEISHIN Ltd.).

Acrylamide Polymer

The acrylamide polymer of the present invention is obtained by polymerizing a monomer including (meth)acrylamide which is obtained by the method for producing an amide compound according to the present invention, and is also a polymer composed of (meth)acrylamide or a copolymer of (meth)acrylamide and at least one unsaturated monomer which is copolymerizable with (meth)acrylamide.

Examples of copolymerizable unsaturated monomers include (meth)acrylamide derivatives such as 2-acrylamide-2-methylpropane sulfonic acid and salt thereof, N-methylolacrylamide, dimethylaminopropyl acrylamide or tertiary ammonium salt thereof, and N,N-dimethylacrylamide; acids such as (meth)acrylic acid, vinyl sulfonic acid, allyl sulfonic acid, and styrene sulfonic acid, or water-soluble salt thereof; lower acrylester derivatives of (meth)acrylic acids such as ethyl acrylate, methyl acrylate, and hydroxypropyl methacrylate; alkyl (methyl or ethyl) aminoalkyl (ethyl or propyl) esters of (meth)acrylic acid or tertiary salts thereof such as N,N-dimethylaminoethyl methacrylate, N,N-diethylaminoethyl, methacrylate, and N,N-dimethylaminoethyl acrylate or tertiary ammonium salts thereof; 2-vinylimidazoline and 2-vinylpyrimidine, or tertiary ammonium derivatives thereof; N-vinylacetamide, vinyl acetate, and vinyl pyrrolidone. As long as water-solubility of the obtained acrylamide polymer is not impaired, water-insoluble or hydrophobic monomers such as acrylonitrile and styrene may be used. A "(meth) acrylic acid" of the present invention is defined as acrylic acid and/or methacrylic acid.

(Method for Producing Acrylamide Polymer)

A method for producing an acrylamide polymer is shown below.

An acrylamide aqueous solution after hydration reaction may be used as it is as (meth)acrylamide, and, if necessary, a concentration process such as an evaporation and concentration process, or a purification process such as an activated carbon process, ion-exchange process, and filtering process may be carried out before polymerization.

Any polymerization methods may be used as long as monomers are polymerized in an aqueous solvent. An adiabatic polymerization system or a sheet polymerization system which is carried out on a belt with heat removal may be selected as needed.

Polymerization temperature is usually 0 to 12° C., and preferably 10 to 90° C.

A monomer concentration when the monomers are polymerized in an aqueous solvent is usually 10 to 90% by mass, and preferably 20 to 80% by mass. When the monomer concentration is 10% by mass or more, high-molecular mass acrylamide polymer is obtained. When the monomer concentration is 90% by mass or less, crosslink reaction during polymerization is prevented and decrease of solubility and insolubilization are suppressed.

As a polymerization initiator, conventional initiators can be used. Examples of polymerization initiators include peroxides such as potassium persulfate, ammonium persulfate, benzoyl peroxide, hydrogen peroxide, and t-butyl hydroperoxide; azo compounds such as azobisisobutylonitrile; photolytic polymerization initiators such as benzoinethylether; reducing agents which form initiators with the above peroxides by redox reaction, such as sodium hydrogen sulfite, sodium sulfite, sodium hydrosulfite, triethanolamine, and ferrous sulfate. These polymerization initiators are used singularly or in combination of two or more according to an ordinary method.

The obtained gel acrylamide polymer is chopped by a chopper such as a meat chopper and then dried. If necessary, the gel acrylamide polymer may be ground by a grinder according to an ordinary method to be a powdery acrylamide polymer dried article. Examples of drying devices include a tray type dryer, a belt dryer, a rotary dryer, a fluidizing dryer, an infrared ray dryer, and a high frequency dryer.

When the acrylamide polymer obtained by the above method is dissolved with 1% by mass concentration in 4% by mass saline solution, 1% by mass salt viscosity measured at 25° C. under 6 RPM using No. 3 rotor is 2000 mPa·s or more, and preferably, 3000 mPa·s (viscosity of 2000 mPa·s corresponds approximately to a molecular mass of acrylamide polymer of ten million).

With regard to solubility of the obtained acrylamide polymer, the amount of gel-insoluble matter retained on the wire gauze is visually observed when acrylamide polymer powder is dissolved with 0.1% by mass concentration in ion-exchanged water and filtering with an 80 mesh wire gauze. Almost no gel-insoluble matter is observed.

The obtained acrylamide polymer has a color tone being almost colorless. Accordingly, the acrylamide polymer is preferably used for coagulants, thickeners for paper making, and the like.

As described above, in the method for producing an amide compound of the present invention, since a positive-displacement pump is used for transferring a liquid including a microbial catalyst and an amide compound, shearing force is not applied to the microbial catalyst and, as a result, generation of impurities derived from the microbial catalyst is suppressed.

Since the acrylamide polymer of the present invention is obtained by polymerizing a monomer including (meth)acrylamide containing few impurities, the acrylamide polymer has high-molecular mass and high solubility, and is almost colorless.

EXAMPLES

The present invention is explained in detail with reference to examples below. In the following examples and comparative examples, "%" means % by mass and "parts" means parts by mass.

Example 1

(1) Preparation of Microbial Catalyst

*Rhodococcus rhodochrous* sp. J-1 (FERM BP-1478) having nitrilehydratase activity was aerobically cultured on a culture medium (pH 7.0) including 2% of glucose, 1% of urea, 0.5% of peptone, 0.3% of yeast extract, and 0.05% of cobalt chloride. After the culture was completed, cultured microorganisms were collected by centrifugation and the collected microorganisms were washed with 50 mM phosphate buffer (pH 7.0). The above buffer was added to the washed microorganisms to obtain a microorganism suspension (when converted as a dried microorganism: 20%), then the microorganism suspension was defined as a microbial catalyst.

(2) Preparation of Acrylamide 32 kg of 0.2 g/L of sodium acrylate aqueous solution was set in a 50 L internal volume reaction tank, then 50 g of the microbial catalyst prepared in (1) was added. The mixture was stirred while controlling to maintain pH 7.0 and 15° C. Acrylonitrile was continuously fed to the mixture so that concentration of acrylonitrile was always maintained at 2%, and the reaction was continued until the concentration of acrylonitrile achieved at 47.3%. Thereafter, feeding of acrylonitrile was stopped and reaction was maintained at 20° C. until acrylonitrile was not detected in the reaction solution.

(3) Filtering Reaction Solution

After completing the reaction, the reaction solution was transferred to a crossflow membrane (MLE 7101 manufactured by KURARAY CO., LTD.) by a NEMO® pump (a screw pump manufactured by HEISHIN Ltd.), crossflow filtration was carried out with the crossflow membrane while circulating the reaction solution by the NEMO® pump at 1.4 to 2 L/min flow rate to separate and remove the microbial catalyst, and as a result, 50% acrylamide aqueous solution was obtained.

(4) Preparation of Acrylamide Polymer 348 parts of 50% acrylamide aqueous solution obtained in (3) and 2 parts of 98% by mass acrylic acid were set in a 1 L beaker, and 400 parts of ion-exchanged water was added to the mixture. Sodium hydroxide was added to the mixture to neutralize the mixture, and thereafter, ion-exchanged water was added so that the total amount became 797 parts. The mixture was transferred to a 1 L Dewar vessel after adjusting temperature of the mixture to 10° C. The solution (mixture) was purged with a nitrogen gas for 30 minutes. 1.5 parts of 10% aqueous solution of 2,2'-azobis(2-amidinopropane) dihydrochloride, 1 part of 0.2% aqueous solution of sodium hydrosulfite, 0.5 parts of 0.2% aqueous solution of t-butyl hydroperoxide were added to the solution as polymerization initiators to start polymerization. Polymerization was adiabatically carried out and a peak temperature was achieved at approximately 74° C. When 30 minutes had passed after achieving the peak temperature, a gel polymer was produced. The gel polymer was cut by scissors to be 5 cm×5 cm×5 cm, and the cut gel polymer was chopped by a 5 mm diameter grating chopper (meat chopper). The chopped gel polymer was dried in a warm air dryer at 60° C. for 16 hours, and then, the dried polymer was ground by a 2 mm diameter grating Wiley grinder. Thereafter, the ground polymer was screened to 0.15 to 1.0 mm particle diameter to obtain acrylamide polymer powder which was a copolymer of acrylamide and acrylic acid.

(5) Evaluation of Acrylamide Polymer

The acrylamide polymer powder obtained in (4) was dissolved in 4% saline solution to be a 1% concentration solution. 1% salt viscosity of the 1% concentration solution was measured by a Brookfield type viscometer at 25° C.

To evaluate water-solubility, the acrylamide polymer powder was dissolved in 5 kg of ion-exchange water to be a 0.1% concentration solution, and subsequently, the solution was filtered with an 80 mesh wire gauze. The amount of gel-insoluble matter retained on the wire gauze was visually observed.

With regard to color tone of the polymer, the acrylamide polymer powder was visually observed. These results are shown in Table 1.

Example 2

Except for exchanging a NEMO® pump for a rotary pump SX2/013/H (manufactured by Alfa Laval K.K.) in the crossflow filtration of the reaction solution, the acrylamide polymer powder was obtained and evaluated by the same procedure as Example 1. The results are shown in Table 1.

Comparative Example 1

Except for exchanging a NEMO® pump for a magnet pump MD (centrifugal pump: manufactured by IWAKI CO., LTD.) in the crossflow filtration of the reaction solution, the acrylamide polymer powder was obtained and evaluated by the same procedure as Example 1. The results are shown in Table 1.

TABLE 1

| | Pump | | Evaluations of acrylamide polymer | | |
|---|---|---|---|---|---|
| | Type | Name | 1% salt viscosity | Solubility | Color tone |
| Example 1 | Screw pump | NEMO ® pump manufactured by HEISHIN Ltd. | 3600 | Good | White |
| Example 2 | Rotary pump | Rotary pump SX2/013/H manufactured by Alfa Laval K. K. | 3580 | Good | White |
| Comparative Example 1 | Centrifugal pump | Magnet pump MD manufactured by IWAKI CO., LTD. | 3400 | Not good | Pale yellow |

In Table 1, evaluation criteria of solubility are as follows.
"Good": gel matter is almost not observed.
"Not good": gel matter is observed.

According to the above results, the acrylamide polymer produced by using, as a raw material, the acrylamide which is obtained by the method for producing an amide compound of the present invention has excellent solubility and colorless color tone.

INDUSTRIAL APPLICABILITY

An acrylamide polymer produced by using, as a raw material, an acrylamide which is obtained by a method for producing an amide compound of the present invention is preferably used for coagulants, thickeners for paper making, and the like.

The invention claimed is:

1. A method for producing an amide compound, comprising:
   reacting a nitrile compound with water in the presence of a microbial catalyst to obtain an amide compound, and
   subsequently transferring a solution containing the microbial catalyst and the amide compound by a rotary pump to obtain the amide compound.

2. The method for producing an amide compound according to claim 1, wherein the nitrile compound is (meth)acrylonitrile and the amide compound is (meth)acrylamide.

3. The method of claim 1, wherein the reacting is conducted at a pH ranging from 5 to 9.5.

4. The method of claim 1, wherein the reacting is conducted at a temperature ranging from 5.5° C. to 50° C.

5. The method of claim 1, wherein the reacting is conducted until the amide constitutes from 30% to 60% by weight of the reaction solution.

6. The method of claim 1, wherein the nitrile compound is continuously fed into the water in the presence of the microbial catalyst.

7. The method of claim 1, wherein the rotary pump is employed only during the transferring step.

8. The method of claim 1, wherein the microbial catalyst is a transformant expressing a nitrilhydratase.

9. The method of claim 8, wherein the transformant is selected from the group consisting of *Escheria coli* MT10770, *Escheria coli* MT10822, and *Rhodococcus rhodochrous*.

10. The method of claim 1, wherein the nitrile compound is acrylonitrile and the amide compound is acrylamide.

* * * * *